United States Patent [19]

Blair et al.

[11] 4,317,885

[45] Mar. 2, 1982

[54] MICROBIOLOGICAL PROCESS FOR REMOVING NON-IONIC SURFACE ACTIVE AGENTS, DETERGENTS AND THE LIKE FROM WASTEWATER AND MICROORGANISM CAPABLE OF SAME

[75] Inventors: James E. Blair, Roanoke; Lois T. Davis, Salem, both of Va.

[73] Assignee: Sybron Corporation, Rochester, N.Y.

[21] Appl. No.: 158,758

[22] Filed: Jun. 12, 1980

Related U.S. Application Data

[62] Division of Ser. No. 35,045, May 1, 1979, Pat. No. 4,274,954.

[51] Int. Cl.³ .............................................. C12N 1/20
[52] U.S. Cl. ................................... 435/253; 435/876; 210/611
[58] Field of Search ................ 435/876, 253; 210/601, 210/610, 611, 612, 620

[56] References Cited

U.S. PATENT DOCUMENTS

| | | | |
|---|---|---|---|
| 3,105,014 | 4/1963 | Harrison | 435/876 X |
| 3,660,278 | 5/1972 | Mimura et al. | 210/611 |
| 3,843,517 | 10/1974 | McKinney et al. | 435/876 X |
| 4,146,470 | 3/1979 | Mohan et al. | 210/601 |

*Primary Examiner*—R. B. Penland
*Attorney, Agent, or Firm*—Sughrue, Mion, Zinn, Macpeak and Seas

[57] ABSTRACT

A process for degrading and removing anionic and/or non-ionic surface active agents, detergents and the like from wastewater containing the same comprising treating wastewater containing the anionic and/or non-ionic surface active agents, detergents and like compounds with a novel microbial strain of *Pseudomonas fluorescens* under aerobic conditions; and the novel microorganism of the strain *Pseudomonas fluorescens*.

1 Claim, No Drawings

MICROBIOLOGICAL PROCESS FOR REMOVING NON-IONIC SURFACE ACTIVE AGENTS, DETERGENTS AND THE LIKE FROM WASTEWATER AND MICROORGANISM CAPABLE OF SAME

This is a Division of application Ser. No. 35,045, filed May 1, 1979, now U.S. Pat. No. 4,274,954.

BACKGROUND OF THE INVENTION

1. Field of the Invention

This invention relates to a process for degrading anionic and/or non-ionic surface active agents, detergents and like materials from wastewater containing the same and, more specifically, to a process for treating waste water containing anionic and/or non-ionic surface active agents, detergents and like materials, for example, effluent from industrial plants, including those from textile manufacturers or processors, with a novel microorganism of the strain *Pseudomonas fluorescens* whereby the anionic and/or non-ionic surface active agents, detergents and similar materials in the wastewater are thereby degraded and removed and the wastewater is purified. Further, this invention relates to a novel microbial strain of the genus Pseudomonas.

2. Description of the Prior Art

Wastewaters containing organic and inorganic materials as pollutants are unsuitable for reuse and undesirable for release into the biosphere due to problems of pollution which results when they are discharged untreated. To remove, or at least minimize, this difficulty, domestic, municipal and industrial wastewaters are conventionally processed in biological treatment systems, for example, aerated lagoons or activated sludge systems, for removal of biodegradable organic matter prior to re-use or discharge to receiving bodies of water.

While the biological processes occurring during such a biological treatment provide the ability to produce effluent with lower biochemical oxygen demand (BOD) and low chemical oxygen demand (COD), unfortunately, removal of materials such as anionic and non-ionic surface active agents, detergents and like materials using conventionally employed biological treatment systems has not met with a large amount of success. Even when the biological treatment system is capable of degrading materials such as anionic and non-ionic surface active agents, detergents and like materials, the degradation process is often too slow or insufficient resulting in a concentration build-up of these materials or a carry through the system of these materials undigested. Reduction in the levels of anionic and non-ionic surface active agents, detergents and similar materials in wastewater to an acceptable level for discharge of the wastewater into the biosphere is either costly or ineffective particularly for difficultly biodegradable or non-biodegradable materials.

The difficulty arising due to the inability of bacteria normally present in conventional biological treatment systems to degrade anionic and non-ionic surface active agents, detergents and like materials at an acceptable rate, if at all, or in reducing the concentration thereof to the extent that such wastewater after treatment can be released into the biosphere has created a problem in the past. This is particularly true where insufficiently treated water containing these materials is released in areas where the water supply is naturally confined or in areas where the water table is particularly high. Numerous federal and state regulations relating to effluent wastewater quality as to surface active agents, detergents and like materials concentrations have been promulgated and implemented to protect the biosphere. In the past decade, numerous changes in the synthetic detergent industry have occurred as a result of this problem with a shift from non-biodegradable surface active agents and detergents to more biodegradable surface active agents and detergents. Although there has been this change to domestic and industrial use of more biodegradable surface active agents and detergents, concern still exists with the treatment of wastewaters containing such.

Even with the shift to more biodegradable synthetic detergents and surface active agents, a problem still exists in the treatment of industrial wastewaters where, due to performance characteristics, synthetic surface active agents and detergents which would basically, in the present state of the art, be considered to be non-biodegradable are still employed resulting in difficulties in wastewater treatment of effluent from these industrial processes utilizing such. In particular, the use of microbiological treatment of wastewater effluents from textile plants employing non-biodegradable synthetic surface active agents and detergents as processing aids and agents has resulted in high cost treatment of such wastewater. Further, the presence of these synthetic surface active agents and detergents in wastewater effluent has caused processing difficulties due to foaming which inherently occurs with increased concentration of such materials in the wastewater effluent. This foaming during treatment of such wastewaters has thus resulted in the need for increased capital outlay to provide larger treatment facilities than would normally be required were the foaming not to exist or has resulted in decreased through-put where capacity of the biological treatment facility is not increased.

With the increasing concern as to minimization of the problems arising from pollution, biological processes utilizing microorganisms are being industrially, municipally and domestically employed and in increasing amount. In the processing of wastewaters a large amount of activity in research and development has occurred and is presently occurring to develop improved microbial strains capable of use in industrial, municipal and domestic wastewater treatment facilities. While advances have been made in curtailing pollution problems arising from synthetic surface active agents and detergents due to the shift to more biodegradable materials, a sufficiently acceptable solution to the problem of removing difficulty biodegradable or substantially non-biodegradable synthetic surface active agents and detergents from wastewaters from domestic, municipal and industrial sources has not yet been developed.

As far as surface active agents are concerned, ethoxylated alkyl phenolics and naphtholics have advantageous properties as surface active agents and detergents and are useful industrially. Unfortunatley, such phenolics and naphtholics, particularly those in which the alkyl moiety is branched chain, are considered in the present state of the art to be non-biodegradable or difficultly biodegradable. As a result, it is necessary to monitor wastewaters from processes in which they are used to ensure that their levels in discharge waters meet municipal, state and federal standards to prevent water pollution.

In view of the industrial utility of these phenolics and naphtholics and the requirements of meeting water pollution regulations on the maximum levels they can be present in discharged waters, an analytical method for determining the levels of such in water is disclosed in *Environmental Science and Technology*, 11, No. 13, p. 1167–1171 (December 1977). The levels of such a nonylphenol ethylene oxide condensate having 10 moles of ethylene oxide per molecule appearing in wastewater which had been biologically treated using semicontinuous activated sludge or continuous activated sludge were determined. This is the only known work where an alkyl phenolic or naphtholic ethylene oxide condensate has been subjected to microbiological treatment with a reduction in the amount thereof being observed. Even here, this biological treatment insufficiently reduced the level of such a phenolic detergent in wastewater and the time required to achieve such was undesirably long.

SUMMARY OF THE INVENTION

Accordingly, an object of this invention is to provide a process whereby anionic and non-ionic surface active agents, detergents, and like materials present in domestic, municipal and industrial wastewaters can be removed.

Another object of this invention is to provide a biological process for treatment of industrial, municipal and domestic wastewaters to not only remove biodegradable organic matter therefrom but to specifically reduce the level of or remove anionic and non-ionic surface active agents, detergents and like materials therefrom.

A further object of this invention is to provide a biological treatment process for removal of difficulty biodegradable or substantially non-biodegradable anionic and/or non-ionic surface active agents, detergents and like materials from industrial, municipal and domestic wastewaters.

Also an object of this invention is to provide a biological treatment process for removal of anionic and/or non-ionic surface active agents, detergents and like materials from industrial, municipal and domestic wastewaters using a novel mutant of *Pseudomonas fluorescens*.

An even further object of this invention is to provide a biological treatment process for industrial, municipal and domestic wastewater to remove anionic and/or non-ionic surface active agents, detergents and like materials therefrom and render such suitable for discharge into the biosphere, thereby minimizing problems of pollution.

An additional object of this invention is to provide a microbiological treatment process capable of degrading anionic and/or non-ionic surface active agents, detergents and like materials, such as the ethylene oxide condensates of alkyl phenolics and naphtholics, which have been previously thought to be substantially non-biodegradable or extremely difficult to biodegrade.

A further object of this invention is to provide a treatment for industrial, municipal and domestic wastewaters utilizing a novel mutant of *Pseudomonas fluorescens*, alone or in combination with other microorganisms, to degrade and remove synthetic anionic and/or non-ionic surface active agents, detergents and like materials from wastewaters.

An additional object of this invention is to provide a novel mutant strain of the species *Pseudomonas fluorescens*.

In one embodiment of this invention, this invention provides a process for treating wastewater containing anionic and/or non-ionic surface active agents, detergents and like materials, which comprises treating wastewater containing synthetic non-ionic surface active agents, detergents and like materials with a microorganism of the strain *Pseudomonas fluorescens* 3P.

In another embodiment of this invention, this invention provides a novel strain of the species *Pseudomonas fluorescens* 3P having the characteristics described below.

DETAILED DESCRIPTION OF THE INVENTION

The novel mutant *Pseudomonas fluorescens* 3P (hereinafter "mutant strain") was produced by selection and subjecting to mutation techniques of strains of microorganisms isolated from the soil and wastewater from a wastewater lagoon at a large textile chemical manufacturing plant located in Wellford, S.C.

This novel mutant strain has been found to be capable of degrading and removing anionic and/or non-ionic surface active agents, detergents and like materials, previously thought to be difficultly biodegradable or substantially non-biodegradable and has the characteristics set forth below.

The mutant strain *Pseudomonas fluorescens* 3P is a gram-negative, non-spore-forming rod. The cells are straight rods which have a single-polar flagellum, and the cells are motile. In culture, approximately 1% of the cells exist in the form of long filaments of greater than five cell units long. On Kings Medium A (described in E. O. King et al., *J. Lab. & Clin. Med.*, Volume 44, No. 2, page 303 (1954), and on Difco BACTO-Antibiotic Medium 3 (trade name produced by Difco Laboratories), solidified with agar at temperatures from 20°–30° C., a fluorescent yellow diffusible pigment is formed. No noticeable odors are given off by cultures of *Pseudomonas fluorescens* 3P on complex media such as nutrient broth and nutrient agar, or minimal salts-based media containing a carbon source such as glucose.

The mutant strain *Pseudomonas fluorescens* 3P is capable of growing on a glucose containing minimal salts medium (Roy Curtiss, III, *J. Bact.*, 89, pages 28–40 (1965)) containing ammonium ion as a nitrogen source, thus demonstrating the strain does not appear to require any growth factor or vitamin supplement. The mutant strain does not utilize acetate as a sole carbon source.

The mutant strain is an obligate aerobe. Growth is not possible anaerobically in the presence of nitrate and the mutant strain does not produce nitrate reductase. The cells of the mutant strain are incapable of accumulating poly-$\beta$-hydroxybutyric acid granules even though DL-hydroxbutyrate serves as a sole carbon source.

A suitable growth temperature range is about 20°–37° C., with optimal growth occurring at 30° C. No growth is observed in ten days at 14° C. The strain displays arginine dihydrolase activity and is incapable of gelatin hydrolysis.

Other cultural characteristics and colonial morphology of this mutant strain are shown in Tables 1–6 below.

In the following tables, *Pseudomonas fluorescens* (ATCC 13525) was employed as a known type strain for characterization purposes.

TABLE 1

MICROSCOPIC MORPHOLOGY

| CHARACTERISTIC | STRAIN | |
|---|---|---|
| | *PSEUDOMONAS FLUORESCENS*** | 3P |
| Cell Size* | | |
| Length | 2.3–2.8 | 2.3–2.8 |
| Width | 0.7–0.8 | 0.7–0.8 |
| Gram Reaction | Negative rod | Negative rod |

*Wet mounts of ten-hour cultures (late exponential phase) viewed under phase contrast (1000×). Sizes given in micrometers.
**Data from Bergey's Manual of Determinative Bacteriology, 8th Ed., The Williams & Wilkins Co., Baltimore (1974).

TABLE 2

COLONIAL CHARACTERISTICS OF *PSEUDOMONAS FLUORESCENS* 3P
After 48 Hours At 35° C.

Plate Count Agar

Slightly irregular colonies are umbonate with a rough surface. They are opaque, four to five mm in diameter and have a slightly undulate edge. They are white in color and no pigments are produced in forty-eight hours.

Nutrient Agar

Circular, convex colonies have a wrinkled surface. They are opaque, three to five mm in diameter and have an undulate edge. Colonies are white and no pigments are produced in forty-eight hours.

Hektoen Enteric Agar

Colonies are circular, convex and have a smooth surface. They are opaque, green, two to three mm in diameter and have an entire edge. No pigments are produced.

Pseudosel Agar

Colonies are irregular, raised, have a smooth surface and an undulate edge. They are one to two mm in diameter, opaque and white in color. A diffusible fluorescent pigment is produced.

T-soy Agar

Circular, slightly convex colonies have a smooth surface and an entire edge. They are two to four mm in diameter, opaque and white in color. A yellow-green diffusible fluorescent pigment is produced.

NOTE:
Plate Count Agar and Hektoen Enteric Agar are products of Difco Laboratories. Pseudosel Agar, Nutrient Agar and Trypticase Soy Agar are products of Baltimore Biological Laboratories.

TABLE 3

UTILIZATION OF CARBON-CONTAINING COMPOUNDS FOR GROWTH

| COMPOUND* | GROWTH RESPONSE** | |
|---|---|---|
| | *PSEUDOMONAS FLUORESCENS* | 3P |
| Carbohydrates (& Sugar Derivatives) | | |
| α-Cellulose | − | + |
| L-Arabinose | − | − |
| D-Ribose | − | − |
| D-Glucose | | + |
| Sucrose | | − |
| Trehalose | | − |
| D-Cellulose | − | + |
| Xylose | − | − |
| Organic Acids | | |
| Acetate | | − |
| Propionate | − | − |
| Bytyrate | | + |
| Isobutyrate | − | − |
| Valerate | − | − |
| Caproate | − | − |
| Heptanoate | − | − |
| Caprate | − | ± |
| Stearate | − | + |
| Dicarboxylic Acids | | |
| Maleate | − | + |
| Malonate | − | − |
| Succinate | − | − |
| Glutarate | − | − |
| Saccharate | − | + |
| Hydroxyacids | | |
| L-Malate | − | − |
| DLβ-Hydroxybutyrate | | + |
| DL-Lactate | − | − |
| DL-Glycerate | + | + |
| Miscellaneous Organic Acids | | |
| Citrate | − | − |
| α-Ketogutarate | − | − |
| Pyruvate | − | + |
| Polyhydric Alcohols and Glycols | | |
| Mannitol | − | − |
| Glycerol | − | + |
| Propyleneglycol | | + |
| m-Inositol | | − |
| Sorbitol | | − |
| Alcohols | | |
| Ethanol | | + |
| n-Propanol | − | + |
| n-Butanol | | + |
| Non-Nitrogenous Aromatic and Other Cylic Compounds | | |
| Benzoate | − | − |
| Aliphatic Amino Acids | | |
| Lα-Alanine | − | + |
| Dα-Alanine | − | + |
| β-Alanine | | + |
| L-Leucine | − | + |
| L-Aspartate | − | + |
| L-Glutamate | + | + |
| L-Lysine | − | + |
| DL-Arginine | | + |
| L-Valine | | ± |
| Glycine | | − |
| Asparagine | | + |
| Amino Acids and Related Compounds Containing A Ring Structure | | |
| L-Histidine | − | + |
| L-Proline | − | + |
| L-Tyrosine | − | − |
| Miscellaneous Nitrogenous Compounds | | |
| Betaine | − | + |
| Sarcosine | − | − |
| Acetamide | − | + |
| Glucosamine | | − |
| Detergents** | | |
| Igepal CO 520 (2000 mg/l) | − | + |
| Igepal CO 610 (2000 mg/l) | − | + |
| Igepal CO 660 (2000 mg/l) | − | + |

*Compound added at 0.5% to minimal salts medium (Curtiss (1965)).
** + indicates growth greater than blank; indicates growth less than that of blank; ± indicates growth approximately equal to blank or weak growth, after seven days at 30° C.
***Trade name for a non-ionic nonyl phenol-ethylene oxide condensate produced by GAF.

TABLE 4
UTILIZATION OF NITROGENOUS COMPOUNDS AS SOLE NITROGEN SOURCE

| | GROWTH RESPONSE** | |
|---|---|---|
| COMPOUND* | PSEUDOMONAS FLUORESCENS | 3P |
| $NH_4Cl$ | − | + |
| $KNO_3$ | − | + |
| L-Glutamate | − | + |
| L-Aspartate | − | ± |
| L-Alanine | − | + |

*Compound added at 0.5 g/100 ml to minimal salts medium (Curtiss (1975) but without $NH_4Cl$ and $NH_4NO_3$) consisting of 0.5 g of D-glucose/100 ml.
** + indicates growth greater than blank; indicates growth less than that of blank; ± indicates growth approximately equal to blank or weak growth, after seven days at 30° C.

TABLE 5
CULTURE GROWTH IN PRESENCE OF HEAVY METALS

| | | STRAIN RESPONSE** | |
|---|---|---|---|
| HEAVY METAL* | CONCENTRATION | PSEUDOMONAS FLOURESCENS | 3P |
| $HgSO_4$ | $2 \times 10^{-3}M$ | − | + |
| | $10^{-3}M$ | − | − |
| | $10^{-4}M$ | − | + |
| | $10^{-5}M$ | − | + |
| $CdCl_2$ | $2 \times 10^{-3}M$ | − | − |
| | $10^{-3}M$ | − | − |
| | $10^{-4}M$ | − | + |
| | $10^{-5}M$ | − | + |
| $CoCl_2$ | $2 \times 10^{-3}M$ | − | − |
| | $10^{-3}M$ | − | − |
| | $10^{-4}M$ | − | + |
| | $10^{-5}M$ | + | + |
| $AgSO_4$ | $2 \times 10^{-3}M$ | − | − |
| | $10^{-3}M$ | − | − |
| | $10^{-4}M$ | − | − |
| | $10^{-5}M$ | − | − |
| $Na_2HAsO_4$ | $2 \times 10^{-3}M$ | − | + |
| | $10^{-3}M$ | − | + |
| | $10^{-4}M$ | − | + |
| | $10^{-5}M$ | − | + |

*Heavy metal added to minimal salts medium containing (0.5%) D-glucose (Curtiss (1965)).
**Growth response scored as: + indicates growth (no inhibition); indicates no growth (inhibition).

TABLE 6
RESISTANCE TO ANTIBIOTICS

| ANTIBIOTIC | STRAIN GROWTH RESPONSE 3P |
|---|---|
| Ampicillin | R* |
| Carbenicillin | R |
| Cephalothin | R |
| Chloramphenicol | R |
| Coly-mycin | S |
| Gentamicin | S |
| Kenamycin | S |
| Mandol | R |
| Streptomycin | I |
| Tobramycin | S |
| Tetracycline | R |
| Amikacin | S |

*Growth response on Pfizer Antimicrobial Susceptibility Disks; Pfizer, Inc. scored: S = sensitive to antibiotic; R = resistance to antibiotic; I = intermediate.

On the basis of the morphological, cultural and physiological characteristics set forth above, the strain has been identified as a member of the species, *Pseudomonas fluorescens* and has been designated herein as *Pseudomonas fluorescens* 3P. A culture of the strain has been deposited in the American Type Culture Collection and has received an accession number, ATCC-31483.

The mutant strain as described above was selected and subjected to mutagenesis techniques in the following manner.

A sample of the soil and wastewater from a large producer of industrial chemicals for the textiles industry was obtained from a lagoon used for holding wastewater effluent from the plant. Several types of microorganisms were isolated from the water sample using an agar medium with 1% by weight of an ethoxylated nonylphenol detergent having 10 moles on the average of ethylene oxide per mole of nonylphenol added thereto (Igepal CO 660) as the only source of carbon. The composition of the media used is set forth in Table 7 below.

TABLE 7
COMPOSITION OF SOLE SOURCE OF CARBON AGAR

| Compound | Quantity |
|---|---|
| $(NH_4)_2SO_4$ | 1.0 g/l |
| $MgSO_4 \cdot 7H_2O$ | 0.2 g/l |
| $KH_2PO_4$ | 1.5 g/l |
| $CaCl_2$ | 10 mg/l |
| $FeSO_4 \cdot 7H_2O$ | 5.0 mg/l |
| $K_2HPO_4$ | 3.5 mg/l |
| $MnSO_4$ | 2.0 ml/l |
| Trace Element Solution | 1.0 ml/l |
| $H_3BO_3$ 10 mg/l | |
| $Li_2SO_4$ 70 mg/l | |
| $MoO_3$ 10 mg/l | |
| Ethoxylated Nonyl-Phenol Detergent (as carbon source) | 1% |
| Agar | 15 g/l |
| pH adjusted to | 7.2 |

Subsequently, to eliminate carryover of nutrient, a second transfer of the microorganisms to agar containing 0.1% by weight of the ethoxylated nonylphenol detergent as described above was conducted.

As a result of the above procedures, eight microorganism cultures showing the heaviest growth were then grown in a liquid medium of the composition shown in Table 7 above (but without the agar). Each of these eight cultures of microorganisms was then subjected to a mutagenesis using 0.02% sodium nitrite at a pH of 6.5-6.8 as described by J. H. Miller, *Experiments in Molecular Genetics*, Cold Spring Harbor Laboratory, New York (1972), in order to stimulate enzymatic changes in the microorganism cultures.

Of the cultures which were treated as described above, those which grew better than the original cultures were then re-inoculated onto an agar medium containing 0.1% by weight ethoxylated nonylphenol detergent as the only source of carbon and then maintained in test tubes containing an aqueous solution of the ethoxylated nonyl phenol detergent in a concentration of 200 mg/l of the ethoxylated nonyl phenol detergent.

Additional cultures were developed by using nonsterile soil percolators. The soil percolators consisted of a side arm suction flask connected to a soil chamber by means of a draft tube through which 50% v/v wastewater fortified with 1.0 g/l $(NH_4)SO_4$ and 3.5 mg/l disodium phosphate and 200 ppm of the ethoxylated nonylphenol was drawn up and allowed to trickle down through the soil media containing the mutated organisms. By this process organisms were further selected and adapted to survive in field conditions. Approximately 75% of the liquid mixture was periodically replaced by fresh solution and this procedure was continued for a six-week period.

At the end of this period of time, three organisms which predominated were isolated from the soil percolators.

All of the microorganism isolates described above were tested for growth on an agar medium containing 200 mg/l of the ethoxylated nonylphenol detergent as the sole source of carbon, on an agar medium containing 200 mg/l of the ethoxylated nonylphenol detergent plus 20% by weight of the wastewater taken from the lagoon of the textile chemical producing plant and tubes of 20% by weight of such wastewater with 200 mg/l of the ethoxylated nonylphenol detergent were added. All of the cultures showed growth in these media.

In order to efficiently remove detergent materials, in 100% industrial wastewater containing such, the cultures obtained as described above were first acclimated to a 40% concentration of such industrial wastewater and then were placed in 100% of such wastewater.

To determine effectiveness in terms of the activity of these cultures, an analysis for nonionics as described by D. G. Stevenson, "The Adsorptiometric Determination of A Non-Ionic Detergent", Dept. of Atomic Energy, Atomic Weapons Research Establishment, Aldermaston, Berkshire, England (August, 1954), was employed.

All of the cultures treated as described above proved to be capable of tolerating 100% of the industrial wastewater. These microorganism cultures were then each inoculated into a 200 mg/l solution of the ethoxylated nonylphenol detergent plus inorganic salts, shown in Table 7 above, in the concentrations set forth in Table 7 (hereinafter "detergent-salts") for further selection as to biodegradation ability.

The three most effective cultures of microorganisms obtained as described above were then inoculated into solutions of 200 mg/l of the "detergent-salts" placed in shake flasks along with a control, and all of the flasks were shaken for a week. The solution contained in each flask was then analyzed for degradation of the detergent using an infrared method of analysis for oil and grease as disclosed in *Standard Methods*, 14th Ed. "Partition-Infrared Method for Grease and Oil", pp. 516–517, American Public Health Association, Washington, D.C. (1975).

The most effective culture for biodegradation of the synthetic detergent described above was found to be a novel strain of the species *Pseudomonas fluorescens* and is designated herein as *Pseudomonas fluorescens* 3P.

The *Pseudomonas fluorescens* 3P can be employed alone or in combination with other microorganisms conventionally used in microbiological treatment of wastes. This invention also includes the use of any variants of *Pseudomonas fluorescens* 3P alone or in combination.

The mutant strain *Pseudomonas fluorescens* 3P used in this invention can be cultured in wastewater from any type of industrial plant containing anionic and/or non-ionic surface active agents, detergents and like materials either using a batch process, a semi-continuous process or a continuous process, and such is cultured for a time sufficient to degrade the anionic and/or nonionic surface active agents, detergents and like materials present in the wastewater and remove them or break them down into components capable of being degraded by other organisms normally found in biological wastewater treatment systems.

The mutant strain of this invention can be employed in ion exchange resin treatment systems, in tricking filter systems, in carbon adsorption systems, in activated sludge treatment systems, in outdoor lagoons or pools, etc. Basically, all that is necessary is for the microorganism to be placed in a situation of contact with the wastewater effluent. In order to degrade the material present in the wastewater, the organisms can be cultured under conditions of about 15° C. to about 42° C., preferably about 20° C. to about 38° C. Desirably, the pH is maintained in a range of about 5.5 to about 8.5, preferably 6.5 to 8.0. Control of the pH can be by monitoring of the system and an addition of appropriate pH adjusting materials to achieve this pH range.

The culturing is conducted basically under aerobic conditions of a dissolved oxygen concentration of about 2 ppm or more, preferably about 5 ppm or more. These conditions can be simply achieved in any manner conventional in the art and appropriate in the treatment system design being employed. For example, air can be bubbled into the system, the system can be agitated, a trickling system can be employed, etc.

The wastewater to be subjected to the process of this invention may contain sufficient nitrogen and phosphorus for culturing without the need for any additional source of nitrogen or phosphorus being added. However, in the event the wastewater is deficient in these two components, suitable available nitrogen sources, such as ammonia or an ammonium salt, e.g., ammonium sulphate, can be added to achieve an available nitrogen content of at least about 10 ppm or more per 100 $BOD_5$. Similarly, phosphorus can be supplemented, if necessary, by addition of orthophosphates, e.g., sodium phosphate, to achieve a phorphorus level in the wastewater of about 1 ppm or more per 100 $BOD_5$. In general, the treatment is conducted for a sufficient time to achieve the reduction in levels of nonionic surface active agents, detergents and like materials and, in general, about 24 hours to eight weeks or longer, although this will depend upon the temperature of culturing, the concentration of these materials in the wastewater and the volume to be treated and other factors, has been found to be suitable.

In the above manner, anionic and/or nonionic surface active agents, detergents and like materials which have been previously considered in the art to be difficultly degradable or non-biodegradable, as well as other organic compounds which might be present in wastewater systems, can be advantageously treated to provide treated wastewater suitable for discharge after any additional conventional processing such as settling, chlorination, etc., into rivers and streams.

As can be seen from an examination of the examples given hereinbelow, the mutant strain *Pseudomonas fluorescens* 3P provides advantageous results in degrading synthetic anionic and non-ionic surface active agents, detergents and the like.

The following description is not to be considered to be limiting, rather merely exemplary of the types of anionic and non-ionic surface active agents, detergents and like materials to which this invention is applicable and which can be degraded in accordance with the method of this invention.

Examples of non-ionic materials include non-ionic alkanolamides; ethoxylated aliphatic alcohols such as ethoxylated lauryl alcohol, ethoxylated coco alcohol, ethoxylated mysteryl alcohol, etc.; ethoxylated alkylphenols and naphthols, such as ethoxylated nonylphenols, ethoxylated dodecylphenol, ethoxylated tetradecylphenol, etc.; polyalkylene oxides such as polyethyleneoxide condensates of varying molecular weights; ethoxylated fatty acids such as ethoxylated stearates, laurates and palmitates, etc.; ethoxylated glycol esters and glycerol esters such as ethoxylated glycosides and glycerides; and similar materials.

Examples of anionic materials include anionic alkyl sulfates such as lauryl sulfate, palmityl sulfate, etc.; alkyl sulfonates such as lauryl sulfonate, etc.; alkylethyleneoxy sulfonates, such as coco alcohol ethyleneoxy sulfonates; sulfosuccinates such as dioctylsulfosuccinate, etc.; alkylbenzene and naphthylene sulfonates such as tetradecylbenzene sulfonate, etc., and like materials.

Most of these types of anionic and non-ionic surface active agents and detergents are well known and are commercially available. Representative examples include Consowet (a dioctylsulfosuccinate anionic detergent produced by Consos, Inc., Charlotte, N.C.), Astrowet (a dioctylsulfosuccinate anionic detergent produced by Astro American Chemical Co., Greenville, S.C.) and Merpol (a non-ionic ethylene oxide condensate produced by E. I. du Pont de Nemours and Co., Inc.) In general, the basic chemical structure or nature of these materials is not limited as long as they can be considered to be anionic or nonionic surface active agents or detergents.

In order to further demonstrate the effectiveness of the strain of *Pseudomonas fluorescens* 3P, the following examples are given as exemplary of the invention but without intending to limit the same. Unless otherwise indicated herein, all parts, percents, ratios and the like are by weight.

EXAMPLE 1

A biotower which was a trickling filter was used. The biotower comprised a reservoir for a liquid and a column containing Pall rings of a plastic resin with one end of the column being placed just above the liquid in the reservoir. A pump was submerged in the liquid reservoir for recycling liquid from the liquid reservoir through a tube to the top of the column for dispersion of the liquid down through the initial Pall ring packing. A synthetic liquid feed comprising 2% by weight sweet whey and 200 mg/l disodium phosphate and inoculated with *Pseudomonas fluorescens* 3P was used and circulated through the biotower in the manner described above until a slime layer of microorganisms formed. A solution of 520 mg/l detergent-salts was fed thereinto on a batch basis. The liquid was then circulated through the biotower for a period of 41.5 hours and samples were removed periodically and analyzed for ethoxylated nonylphenol having 10 moles of ethylene oxide per mole of nonylphenol.

The results showed that from an initial ethoxylated nonylphenol detergent concentration of 520 mg/l, such concentration was reduced to 65 mg/l after 41.5 hours, a degree of removal of 88%.

EXAMPLE 2

A sample of a culture of the mutant strain *Pseudomonas fluorescens* 3P, along with a control, was inoculated into a shake flask containing 200 mg/l of the "detergent-salts" and the shake flask containing the microorganism and the control shake flask were each shaken for one week.

Thereafter, the liquid in each shake flask was analyzed for ethoxylated nonylphenol detergent and the following results in Table 8 were obtained.

TABLE 8

| Sample | Detergent Concentration Initial | Final | % Detergent Degradation |
|---|---|---|---|
| 3P | 200 | 120 | 40 |
| Control | 200 | 200 | 0 |

EXAMPLE 3

The procedures of Example 2 were repeated using a wastewater obtained from the lagoon of a textile chemical producing plant fortified with 200 mg/l of ethoxylated nonylphenol were repeated, again also using a control.

After one week, the ethoxylated nonylphenol concentration had been reduced to 143 mg/l whereas in the control, the ethoxylated nonylphenol detergent concentration was 193 mg/l, substantially the same as that of the initial concentration of ethoxylated nonylphenol. Thus, the *Pseudomonas fluorescens* 3P microorganism accomplished a biodegradation of 25% more of the ethoxylated nonylphenol detergent than that achieved in the control.

EXAMPLE 4

Experimentation was performed to demonstrate the effectiveness of degradation of Tide (trademark for a household detergent containing an anionic detergent produced by the Proctor and Gamble Co.) by *Pseudomonas fluorescens* 3P.

Two-hundred-fifty ml shake flasks containing 100 mg of Tide/100 ml nutrient broth were used. After seven days, *Pseudomonas fluorescens* 3P had degraded approximately fifty percent of the Tide present. Another flask as a control inoculated simply with a microorganism of a Bacillus species showed poor, if any growth.

Analysis was performed by the methylene blue active substances method (14th Edition, *Standard Methods for the Examination of Water and Wastewater*, 1975), with the exception that the standard curve in the method was made using Tide in place of the linear alkylate sulfonate.

While the invention has been described in detail and with respect to specific embodiments thereof, it will be apparent to one skilled in the art that changes and modifications can be made therein without departing from the spirit and scope thereof.

What is claimed is:

1. A biologically pure culture of the microorganism *Pseudomonas fluorescens* 3P having the identifying characteristics of ATCC-31483, said microorganism upon culturing in wastewater containing a material selected from the group consisting of anionic surface active agents, nonionic surface active agents, detergents and mixtures utilizes said material as an assimilable source of carbon.

* * * * *